United States Patent [19]

Kaufman

[11] 4,294,822

[45] Oct. 13, 1981

[54] 5-AMINOALKYL-4,4,8-TRIALKYLPSORALENS

[75] Inventor: Kurt D. Kaufman, Kalamazoo, Mich., by Marilee Kaufman, conservator

[73] Assignee: Thomas C. Elder, Inc., Hamilton, Ind.

[21] Appl. No.: 173,437

[22] Filed: Jul. 29, 1980

[51] Int. Cl.$^3$ .................. C07D 493/02; A61K 31/365
[52] U.S. Cl. ................... 424/59; 260/343.21; 424/281; 424/279
[58] Field of Search ............. 260/343.21, 343.3 R; 424/59, 281, 279

[56] References Cited

U.S. PATENT DOCUMENTS 4,169,204  9/1979  Hearst et al. ............ 260/343.21

OTHER PUBLICATIONS

Hearst et al., *Chemical Abstracts*, vol. 87, entry 78962f (1977).
Dawber, *J. Soc. Cosmet. Chem.* vol. 28, pp. 403–406 (1977).
Martins et al., *Chemical Abstracts*, vol. 81 entry 99676g (1974).
Shen et al., *Chemical Abstracts*, vol. 88 entry 59494j (1978).
Johnston et al., *Chemical Abstracts*, vol. 87 entry 147284a (1977).
Isaacs et al., *Chemical Abstracts*, vol. 86 entry 135108n (1977).

*Primary Examiner*—John M. Ford
*Attorney, Agent, or Firm*—Gordon W. Hueschen

[57] ABSTRACT

The invention relates to 5'-aminoalkyl-4',4,8-trialkylpsoralens having enhanced photosensitizing activity, especially oral and topical activity, as well as low toxicity, when compared with psoralens of different structure.

6 Claims, No Drawings

5′-AMINOALKYL-4,4′,8-TRIALKYLPSORALENS

BACKGROUND OF INVENTION

1. Field of Invention

Psoralens, photochemotherapy, psoralens having enhanced photosensitizing activity for use in photochemotherapy.

2. Prior Art

Psoralens have been used for years as dermal photosensitizing agents, e.g., in the treatment of vitiligo. Their topical and/or oral application, followed by irradiation with light, results in stimulation of melanin, thus producing a tanning effect. They have accordingly also been used for such cosmetic purpose. More recently, psoralens have been found useful in the photochemotherapeutic treatment of psoriasis, in which case they are administered orally or topically to the subject, whose skin is subsequently exposed to controlled ultraviolet radiation, as in a Psoralite (TM) apparatus. A high percentage of remissions of this disease have been effected in such manner.

The effectiveness of a psoralen for such uses and for such purpose is at least partially related to its ability to produce erythema upon the skin upon irradiation. Psoralens also have other uses, and their uses, as well as underlying rationale and theory, are partially elucidated in U.S. Pat. No. 4,124,598, and are otherwise well-known in the art from various preexisting publications.

With the increasing emphasis on photochemotherapeutic treatments for various purposes using psoralens and controlled application of ultraviolet light, the requirements for optimally-effective photosensitizing psoralens have become more apparent. To eliminate the necessity of excessive and perhaps dangerous ultraviolet light applications or dosages, maximum photosensitization is one obvious criterion. However, to eliminate excessive periods of waiting before photochemotherapy can be commenced, rapid onset of photosensitization upon topical or oral administration of the photosensitizing agent is also of significance. Long or extended action is another criterion of significance in some cases, as when irradiation cannot be applied without some period of delay. Thus, the criteria of rapid onset, early maximization, and extended period of photosensitization action or effect are established as desirable criteria for the photosensitizing agent in this relatively new but rapidly-expanding field of photochemotherapy, certainly of equal importance as contrasted to the single previously-important criterion of high maximum photosensitization activity alone.

The recently-developed 4′-aminomethyl-4,5′,8-trimethylpsoralen appears to be characterized by a high order of oral photosensitizing activity, but exhibits a high degree of toxicity. A low toxicity is, of course, essential. The compounds 5′-aminomethyl-4′-methylpsoralen and 8-aminomethylpsoralen, on the other hand, are essentially inactive orally, apparently due to absence of the 4-methyl group, thus making the photosensitizing activity even more unpredictable than ever in the area and immediate vicinity of the present invention.

OBJECTS OF THE INVENTION

It is an object of the invention to provide novel psoralen compounds. It is a further object to provide novel psoralen compounds which have enhanced characteristics when compared with psoralen compounds of different structure. It is an additional object to provide novel psoralen compounds having enhanced photosensitizing characteristics in accord with the foregoing stated criteria. It is a still further object to provide novel psoralen compounds having enhanced photosensitizing characteristics and relatively low toxicity, and of a structure differing essentially from known psoralen compounds, the advantageous properties of which could not be predicted on a basis of any known structure-activity relationships. Still other objects will be apparent to one skilled in the art and still additional objects will become apparent hereinafter from the following description and claims.

SUMMARY OF THE INVENTION

The present invention relates to 5′-aminoalkyl-4′,4,8-trialkylpsoralens having enhanced photosensitizing activity, especially oral activity, including early onset, increased maximum, and extended duration of activity, as well as low toxicity, when compared with psoralens of different structure. Despite their different structure, the compounds are nevertheless characterized by excellent and superior photosensitization activity according to the aforesaid various criteria, as well as relatively low toxicity. The invention is particularly concerned with 5′-primaryaminoloweralkyl-4′,4,8-triloweralkylpsoralens and especially 5′-aminomethyl-4,4′,8-trimethylpsoralen.

The compounds of the invention have the formula

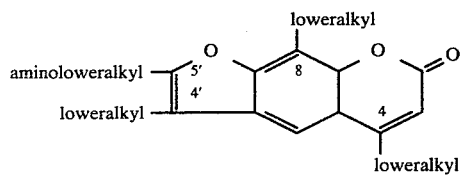

5′-primaryaminoloweralkyl-4′-loweralkyl-4-loweralkyl-8-lower-alkylpsoralen, wherein loweralkyl is preferably methyl.

DETAILED DESCRIPTION OF THE INVENTION

The following Preparations and Examples are given by way of illustration only and are not to be construed as limiting.

Appropriate starting umbelliferones (4-alkyl and 4,8-dialkyl-7-hydroxycoumarins) are known compounds which can be prepared in known manner and converted to a variety of alkylsubstituted psoralens by known procedure (MacLeod and Worth, Tetrahedron Lett., 237–240(1972)). Selected variations in the starting 4(and 8) alkyl substituents and in the alkylhalomethyl ketone reactants produce the known 4,4′,8-trimethylpsoralen, and/or variations in the alkyl group at positions 4,4′ and 8 of the resulting psoralen, as will appear more fully hereinafter, especially from the Examples which follow. Chloroalkylation with a selected α-chloroalkyl methyl ether introduces a desired and preselected chloroalkyl group into the 5′ position of the 4′,4,8-trialkylpsoralen nucleus, whereafter reaction with potassium phthalimide followed by cleavage with hydrazine hydrate (hydrazinolysis) yields the desired 5′-aminoalkyl-4′,4,8-trialkylpsoralen, in which the various alkyl groups correspond to those in the starting 4,8-dialkyl-7-hydroxycoumarin, the alkylhalomethyl ketone, and the chloroalkylating agent employed. Alternatively, the haloalkylation may be effected according to Olah and Kuhn, J. Org. Chem. 29, 2317 (1964) or Friedel-Crafts and Related Reactions, Vol. II, Part 2, G. A. Olah, ed., Interscience, New York, N.Y., 1964, page 749. The structure of the final 5'-aminoalkyl-4',4,8-trialkylpsoralen is confirmed by nuclear magnetic resonance spectra, using a Perkin Elmer Model R-24B and elemental analysis. Melting points are uncorrected.

5'-AMINOMETHYL-4',4,8-TRIMETHYLPSORALEN

5'-Chloromethyl-4,4',8-trimethylpsoralen. To a solution of 4,4',8-TMP (29.36 g, 0.13 mol) in glacial acetic acid (1.3 L) was added chloromethyl methyl ether (200 mL) at room temperature. After 48 hours a white precipitate had formed and was filtered. The crystals were air-dried to obtain 28.63 g (80%) of 5'-chloromethyl-4,4',8-trimethylpsoralen; mp 169°–171° C.; NMR ($CDCl_3$) $\delta$ 2.29 (s, 3H), 2.46 (s, 3H), 2.54 (s, 3H), 4.67 (s, 2H), 6.14 (s, 1H), 7.3 (s, 1H).

5'-N-Phthalimidomethyl-4,4',8-trimethylpsoralen. A solution of 5'-chloromethyl-4,4',8-trimethylpsoralen (13.63 g, 0.05 mol) and potassium phthalimide (11.1 g, 0.06 mol) in dimethylformamide (1.4 L) was stirred at 100° C. for 6 hours. After cooling and diluting with water (3.0 L), the precipitate was collected and dried to obtain 17.95 g (92.7%) of 5'-N-phthalimidomethyl-4,4',8-trimethylpsoralen.

5'-Aminomethyl-4,4',8-trimethylpsoralen. A mixture of 5'-N-phthalimidomethyl-4,4',8-trimethylpsoralen (17.95 g, 0.046 mol), hydrazine hydrate (21.2 mL) and 95% ethanol (2 L) was heated under reflux for 6 hours and concentrated on a rotary evaporator to a residue which dissolved in 0.1 N NaOH (4.0 L). Three portions (300 mL) of $CHCl_3$ extracted 5.8 g (49%) of a yellow solid, mp 193°–201° C. The solid was sublimed at 179° C. for 36 hours to yield 2.5 g of material which, after recrystallization from benzene/ligroin, gave 1.9 grams of more highly purified material; mp 197°–199° C.; NMR ($CDCl_3$) $\delta$ 1.7 (broad s, 2H), 2.21 (s, 3H), 2.44 (s, 3H), 2.48 (s, 3H), 3.93 (s, 2H), 6.15 (s, 1H), 7.35 (s, 1H). The product was subjected to elemental analysis and found to be 5'-aminomethyl-4,4',8-trimethylpsoralen.

Anal. Calcd. for $C_{15}H_{15}NO_3$: C, 70.02; H, 5.88; N, 5.44. Found: C, 69.74; H, 6.14; N, 5.68.

5'-AMINOETHYL-4'-ETHYL-4,8-DIMETHYLPSORALEN

In the same manner as given in the foregoing, but using 4'-ethyl-4,8-dimethylpsoralen and $\alpha$-chloroethyl methyl ether in Step 1, the title compound is produced.

5'-AMINOMETHYL-4',8-DIMETHYL-4-PROPYLPSORALEN

In the same manner as given in the foregoing, but using 4',8-dimethyl-4-propylpsoralen in Step 1, the title compound is produced.

5'-AMINOMETHYL-4',4-DIMETHYL-8-ETHYLPSORALEN

In the same manner as given in the foregoing, but starting from 4',4-dimethyl-8-ethylpsoralen in Step 1, the title compound is produced.

In the same manner as given in the foregoing, other variations in selection of starting materials are productive of still other 5'-aminoloweralkyl-4',4,8-triloweralkylpsoralens within the scope of the invention in which one, two, or all of the loweralkyl groups present in the compound are varied. As used herein, the term "loweralkyl" comprehends such straight or branched radicals or groups having one to eight carbon atoms, preferably one to four carbon atoms, inclusive, such as methyl, ethyl, propyl, isopropyl, butyl, and the like.

The 5'-aminomethyl-4'-methylpsoralen was made in the same manner, starting from 7-hydroxycoumarin, for comparison purposes. The final step of its preparation follows A mixture of 4'-methyl-5'-phthalimidomethylpsoralen (6.0 g; 16.7 mmol), absolute ethanol (1.2 L), glacial acetic acid (15.24 mL, 266 mmol), and 85% hydrazine hydrate (7.63 mL, 133 mmol) was heated under reflux for six hours and concentrated in vacuo to an off-white solid. HCl (1 F, 500 mL) was added, followed by $NaHCO_3$(s) until the pH was ca. 8.0, and the mixture was extracted with three portions (500 mL) of $CHCl_3$, which were dried ($Na_2SO_4$), and concentrated in vacuo to obtain 5'-aminomethyl-4'-methylpsoralen (2.945 g, 77%), mp 153.1°–156.3° C. Recrystallization from a benzene-ligroin (bp 94°–105°) solvent pair gave an analytical sample (73% recovery), mp 154.1°–156.1° C. NMR ($CDCl_3$) $\delta$1.7 (br s, 2, $NH_2$, exchangeable with $D_2O$), 2.25 (s, 3, 4'-$CH_3$), 3.95 (s, 2, $CH_2$), 6.31 (d, 1, J=9 Hz, $C_3H$), 7.32 (s, 1, $C_8H$), 7.46 (s, 1, $C_5H$), 7.75 (d, 1, J=9 Hz, $C_4H$).

Anal. Calcd. for $C_{13}H_{11}O_3N$: C, 68.11; H, 4.84; N, 6.11. Found: C, 67.94; H, 4.85; N, 5.82.

PHARMACOLOGY

The biophotosensitization activity of the compounds of the present invention was determined by visual grading of erythemal response according to a modification of the procedure of Pathak and Fitzpatrick, J. Invest. Dermatol. 32, 509–518 (1959), entitled "Bioassay of Natural and Synthetic Furocoumarins (Psoralens)". (The psoralens are of course "linear" isomers of the furocoumarin family.) According to this bioassay of photosensitizing potency, erythema production on albino guinea pig skin is measured visually and the response accorded a gradation definition according to a 0, $\mp$, 1, 2, 3, and 4 scale. The modification employed involved variation of the time between administration of the test compound and exposure to ultraviolet light, thereby enabling measurement of times of onset and decline of the induced photosensitivity effect.

PROTOCOLS

Topical: Each drug is tested topically at a concentration of one percent (1%) in ethanolic solution. Test sites of one square centimeter of skin each receive one-tenth milliliter of a particular selected test solution thirty minutes prior to exposure to two joules of ultraviolet "A" radiation. Three animals of fifteen in each group of guinea pigs are tested with each product to arrive at an average response designated "Reaction Intensity" which is determined by observation and grading 24 hours and 48 hours after administration.

Oral: Each drug is tested orally by administering a dosage of forty (40) mg/kgm of body weight to groups of fifteen guinea pigs. The appropriate dosage for each animal is packed into a gelatin capsule and placed far back in the animal's pharynx. Swallowing is assisted by syringe delivery of three milliliters of water. The animals are not allowed to eat or drink six hours before and after administration of each product. The exposure to ultraviolet "A" radiation is at a dose of two joules per square centimeter at different times after administration, e.g., 10, 20, 30, 45, 60, 90, 120, 180, 240 and 360 minutes after administration. Readings and evaluations are carried out 48 hours post ingestion. When a particular product is exceptionally active in the test, the per os dosage may of course be halved, halved again, or otherwise reduced.

Gradation: Responses are graded as follows:

0 No response; ± faint erythema; 1+ erythema; 2+ erythema and slight edema; 3+ erythema and intense edema; and 4+ vesiculobullous reaction.

RESULTS

The compounds of the invention show some erythematic topical activity as read at both 24 and 48 hours. They show oral activity as read at 48 hours which is outstanding, with high maxima, almost immediate onset, and long duration of photosensitizing effect. The compound 5'-aminomethyl-4',4,8-trimethylpsoralen is particularly outstanding, maintaining vesiculobullous response beyond 240 and through 360 minutes, with an early onset of intense erythema at only 10 minutes, maintaining the maximum from 30 minutes through 360 minutes. It was only slightly less active at 20 mg/kg, and still of interest due to its quick, great and prolonged activity, even at 10 mg/kg. It is far superior in photosensitizing maximum, onset to maximum, and duration of maximum when compared with 4'-aminomethyl-4,5',8-trimethylpsoralen. Its photosensitizing efficiency is still superior in all respects at the quartered oral dosage of 10 mg/kgm. In contrast, the 5'-aminomethyl-4'-methylpsoralen (made as illustrated from 7-hydroxycoumarin) shows essentially no photosensitizing response orally, although it exhibits a 1+, 2+ topical response at 24 and 48 hours. The compounds of the invention show no oral toxicity, no animals dying at any of the dosage levels tested. In contrast, the compound 4'-aminomethyl-4,5',8-trimethylpsoralen shows a high order of oral toxicity, a large number of the animals receiving 40 mg/kgm thereof dying during the period of their observation, the LD50 for that particular compound apparently being much less than this dosage level.

The biophotosensitization activity of the compounds of the invention is substantial in the erythemal response test according to the procedure of Pathak and Fitpatrick, J. Invest. Dermatol., 32, 509-518 (1959), entitled "Bioassay of Natural and Synthetic Furocoumarins (Psoralens)", and usually employed standard modifications thereof, as reported hereinbefore. As "biophotosensitization activity" is employed herein, however, as well as "photochemical sensitivity on the skin of a mammal", and "photosensitizing" or "photosensitization", as well as "photochemotherapy", the compounds of the invention are also active biophotosensitizing agents from another standpoint, inasmuch as they produce functional addition in the standard tests for DNA photoreactivity. See, for example, Science 1977, 197 (4306), 906-908; J. Mol. Biol. 1977, 116(4), 661-679; Biochemistry 1977, 16 (6), 1058-1064, and related publications. The compounds are thus clearly useful in the further study of reactions and secondary structures of nucleic acids, and as inhibitors of RNA replication, and are indicated for employment in the inactivation of viruses as well as in the photochemotherapy of psoriasis by the PUVA procedure, in which they are found to be equally as effective as numerous previously-employed psoralen compounds. Their effectiveness is of course dependent upon numerous factors, such as amount of irradiation employed, dosage of the photosensitizing agent, mode of employment (whether topical or oral), and individual skin sensitivities of the mammal subjected to the PUVA therapy, including of course human beings, with respect to which psoriasis is a unique malady. The compounds are accordingly useful for all of the foregoing purposes, but particularly for effecting photochemical sensitivity on the skin of a mammal, these terms as employed herein not being restricted to the production of erythema thereon. They are effective both orally and topically, and the method of effecting photochemical sensitivity on the skin of a mammal merely comprises the step of orally or topically administering to the said mammal an effective photosensitizing dose of a compound of the invention. When the subject is then exposed to ultraviolet radiation, more particularly ultraviolet "A", in the non-burning range, functional adducts with DNA are formed and psoriasis is mitigated in human patients, as aforesaid. Other uses of the compounds of the present invention are also set forth in the foregoing.

The pharmaceutical compositions according to the present invention are suitable for use in effecting photochemical sensitivity on the skin of a mammal, particularly a human patient or subject, and comprise an effective amount of a compound of the invention in association with a pharmaceutically-acceptable carrier or diluent. Such compositions are well-known in the art, and reference may again be made to U.S. Pat. Nos. 4,124,598 and 4,130,568 for representative examples and disclosure concerning the same. The procedure for preparation of such compositions is totally conventional in the art. For oral treatment of psoriasis, the active ingredient is generally formulated in tablets or in gelatin capsules. In such case the diluent may, if desired, be eliminated, although it is generally present. For topical application, solutions or ointments may be prepared and employed. These may be formulated with any one of a number of pharmaceutically-acceptable carriers, as is well known in the art. Administration may be, for example, in the form of tablets, capsules, powders, syrups, or solutions, or as already stated in the form of ointments, creams, or solutions for topical use. For tablet preparation, the usual tablet adjuvants such as cornstarch, potato starch, talcum, magnesium stearate, gelatin, lactose, gums, or the like may be employed, but any other pharmaceutical tableting adjuvants may also be used, provided only that they are compatible with the active ingredient. In general, an oral dosage regimen will include about 5 mg. to about 50 mg. per kg. of body weight, with a dose in the neighborhood of about 5–10 mg. per kg. generally being preferred. Such administration and selection of dosage and unit dosage will of course have to be determined according to established medical principles and under the supervision of the physician in charge of the PUVA therapy involved. For topical use, only an effective amount of the active ingredient per unit area is involved, and this will illustratively be in the form of a one percent solution, suspension, or ointment thereof, illustratively applied on the order of one-tenth milliliter per square centimeter, in association with a suitable carrier, e.g., ethanol, or other carrier of types already mentioned.

The amines of the present invention may conveniently be employed in the form of their pharmaceutically-acceptable acid addition salts. When isolating compounds of the invention in the form of an acid addition salt, the acid is preferably selected so as to contain an anion which is non-toxic and pharmacologically acceptable, at least in usual therapeutic doses. Representative salts which are included in this preferred group are the bicarbonates, hydrochlorides, hydrobromides, sulphates, acetates, phosphates, nitrates, methanesulphonates, ethanesulphonates, lactates, citrates, tartrates or bitartrates, and maleates. Other acids are likewise suitable and may be employed if desired. For example, fumaric, benzoic, ascorbic, succinic, salicylic, bismethylenesalicylic, propionic, gluconic, malic, malonic, mandelic, cinnamic, citraconic, stearic, palmitic, itaconic, glycolic, benzenesulphonic, and sulphamic acids may also be employed as acid addition salt-forming acids.

It is to be understood that the invention is not to be limited to the exact details of operation or exact compounds, compositions, methods, or procedures shown and described, as obvious modifications and equivalents will be apparent to one skilled in the art.

I claim:
1. 5'-primaryaminoloweralkyl-4',4,8-triloweralkylpsoralen.
2. A compound of claim 1 which is 5'-aminomethyl-4',4,8-trimethylpsoralen.
3. The method of effecting photochemical sensitivity on the skin of a mammal comprising the step of orally administering to the said mammal an effective photosensitizing dose of a compound of claim 1.
4. The method of claim 3 wherein the compound is 5'-aminomethyl-4',4,8-trimethylpsoralen.
5. A pharmaceutical composition suitable for use in effecting photochemical sensitivity on the skin of a mammal comprising an effective amount of a compound of claim 1 and a pharmaceutically-acceptable carrier of diluent.
6. The composition of claim 5 wherein the compound is 5'-aminomethyl-4',4,8-trimethylpsoralen.

* * * * *

UNITED STATES PATENT AND TRADEMARK OFFICE
CERTIFICATE OF CORRECTION

PATENT NO. : 4,294,822
DATED : October 13, 1981
INVENTOR(S) : Kurt D. Kaufman

It is certified that error appears in the above—identified patent and that said Letters Patent is hereby corrected as shown below:

Col. 2, in the formula, to the right of the eight, place a bond;

" 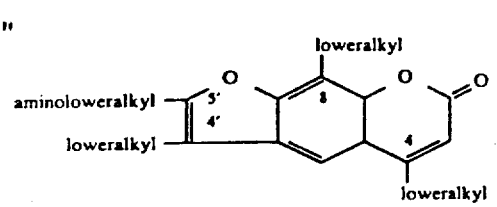 should read " 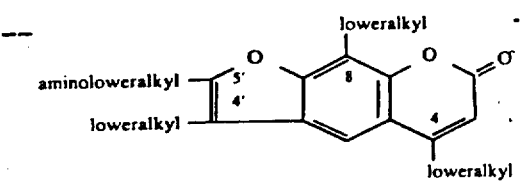

Signed and Sealed this

Fifteenth Day of November 1983

[SEAL]

Attest:

GERALD J. MOSSINGHOFF

Attesting Officer

Commissioner of Patents and Trademarks